United States Patent
Hörndler et al.

(10) Patent No.: US 7,712,961 B2
(45) Date of Patent: May 11, 2010

(54) METHODS AND SYSTEMS FOR IMPROVING 3D VOLUME RECONSTRUCTION FROM 2D X-RAY IMAGES

(75) Inventors: Klaus Hörndler, Nürnberg (DE); Wolfgang Kränzel, Fürth (DE); Christof Fleischmann, Möhrendorf (DE)

(73) Assignee: Ziehm Imaging, GmbH, Nuremberg (DE)

( * ) Notice: Subject to any disclaimer, the term of this patent is extended or adjusted under 35 U.S.C. 154(b) by 0 days.

(21) Appl. No.: 11/594,706

(22) Filed: Nov. 6, 2006

(65) Prior Publication Data

US 2007/0140438 A1 Jun. 21, 2007

(30) Foreign Application Priority Data

Nov. 5, 2005 (DE) .................... 10 2005 052 787

(51) Int. Cl.
*G01D 18/00* (2006.01)
(52) U.S. Cl. ...................................... 378/207
(58) Field of Classification Search ............ 378/4, 378/205, 207, 901
See application file for complete search history.

(56) References Cited

U.S. PATENT DOCUMENTS

| | | | | |
|---|---|---|---|---|
| 5,442,674 A | * | 8/1995 | Picard et al. ................ | 378/20 |
| 5,706,324 A | * | 1/1998 | Wiesent et al. ............. | 378/4 |
| 5,835,563 A | | 11/1998 | Navab et al. | |
| 6,092,928 A | * | 7/2000 | Mattson et al. ............ | 378/205 |
| 6,196,715 B1 | * | 3/2001 | Nambu et al. .............. | 378/197 |
| 6,206,566 B1 | * | 3/2001 | Schuetz ...................... | 378/205 |
| 6,359,959 B1 | * | 3/2002 | Butler et al. ................ | 378/20 |
| 6,359,960 B1 | * | 3/2002 | Wahl et al. .................. | 378/20 |

(Continued)

FOREIGN PATENT DOCUMENTS

| | | |
|---|---|---|
| DE | 100 47 382 | 5/2002 |
| DE | 102 02 091 | 8/2003 |

OTHER PUBLICATIONS

Hein et al., Distortion Correction Table Compression for Volume X-ray CT Applications, In Medical Imaging 2000: Physics of Medical Imaging, Proceedings of SPIE, vol. 3977, 2000.*

*Primary Examiner*—Edward J Glick
*Assistant Examiner*—Alexander H Taningco
(74) *Attorney, Agent, or Firm*—Knobbe Martens Olson & Bear, LLP

(57) ABSTRACT

A method of improving the volume reconstruction in navigationally guided operations is provided. In certain implementations, a phantom which contains X-ray positive marks and marks detectable by a position detection system in a fixed spatial relation to each other is positioned in the region of the volume being investigated on the subject. For the volume reconstruction, a series of 2D X-ray projection images can be created, each of them containing, alongside the structures of the subject being examined, the images of the X-ray positive marks of the phantom as image information. Each 2D data set is transformed by a familiar method, in which, for example, the mechanical deviations of a real-world C-arm type X-ray diagnostic machine are identified by a kinematic model and are corrected. The transformed 2D data can be used for the volume reconstruction, and the volume model with the position information of the X-ray positive marks is relayed to a navigation system.

2 Claims, 1 Drawing Sheet

U.S. PATENT DOCUMENTS

| | | | |
|---|---|---|---|
| 6,466,638 B1 * | 10/2002 | Silver et al. | 378/4 |
| 6,491,430 B1 * | 12/2002 | Seissler | 378/207 |
| 6,690,761 B2 * | 2/2004 | Lang et al. | 378/56 |
| 6,845,142 B2 * | 1/2005 | Ohishi | 378/8 |
| 6,851,855 B2 * | 2/2005 | Mitschke et al. | 378/207 |
| 6,932,506 B2 * | 8/2005 | Mitschke et al. | 378/207 |
| 7,010,095 B2 | 3/2006 | Mitschke et al. | |
| 2004/0013240 A1 * | 1/2004 | Mitschke et al. | 378/205 |
| 2005/0094771 A1 * | 5/2005 | Basu et al. | 378/207 |
| 2005/0117708 A1 * | 6/2005 | Cho et al. | 378/164 |

* cited by examiner

METHODS AND SYSTEMS FOR IMPROVING 3D VOLUME RECONSTRUCTION FROM 2D X-RAY IMAGES

CROSS-REFERENCE TO RELATED APPLICATIONS

This Application claims the benefit of the German Application DE 10 2005 052 787.6 filed Nov. 5, 2005, which is hereby incorporated by reference in its entirety.

BACKGROUND OF THE INVENTION

1. Field of the Invention

This invention generally relates to medical diagnostic imaging systems, and in particular, relates to methods and systems for improving three-dimensional volume reconstructions from two-dimensional x-ray images in navigationally guided operations making use of an X-ray diagnostic machine.

2. Description of the Related Art

Medical operations on living subjects are increasingly being done with navigational support systems. Such systems typically involve the guiding of an instrument by means of a position detection system relative to a tissue region of the subject undergoing treatment. Of special interest is navigation in regions not amenable to the visual inspection of the surgeon, because, for example, the instrument has been introduced inside of the subject. Under these circumstances, the instrument, such as a catheter, is guided in a virtual 3D volume, which has been generated by means of a projection method before or during the operation. A frequent application is to use an X-ray diagnostic machine to generate a series of 2D projection images of a known projection geometry and then to generate a 3D volume data set from these 2D images. The volume data set is relayed to a navigation system, which has a position detection system for marks which can be detected in this way.

In order to make possible high-precision navigation, the system of coordinates of the position detection system can be adjusted to the coordinate system of the 3D volume data set. This process is usually known as registration. During registration, for example, one often uses a phantom which contains X-ray positive marks and marks detectable by a position detection system in a fixed spatial relation to each other. To improve the precision of a reconstructed 3D data set from 2D X-ray projection images, there are known methods which allow for the deviations of the parameters of the projection geometry from the actual projection geometry, influenced, for example, by mechanical torsions of the X-ray diagnostic machine. For this, an X-ray diagnostic machine is "calibrated" by using a special X-ray phantom. Such a calibration is generally done only before being shipped from the factory, after a repair with replacement of mechanical components, or before the start of an investigation.

German patent DE 102 02 091 A1 discloses a device and method for determining a coordinate transformation by using a phantom, on which X-ray positive marks and marks detectable by a position detection system are arranged in a fixed spatial relation to each other. During a scan to create 2D X-ray projection images, the coordinates of the X-ray positive marks are determined in the reconstructed 3D volume and relayed to the position detection and navigation system for adjustment.

U.S. Pat. No. 5,442,674 A and German Patent 199 47 382 C2 disclose known X-ray phantoms by means of which the mechanical insufficiencies of the X-ray diagnostic machine are corrected in a calibration process outside of a surgical use.

U.S. Pat. No. 5,835,563 A concerns an X-ray phantom that remains firmly connected to the patient during an X-ray exam and improves the accuracy of the representations during digital subtraction angiography (DAS).

Certain embodiments of the present invention are adapted to improve the intraoperative volume reconstruction during navigationally guided operations by using an X-ray diagnostic machine and a position detection system in a simple and cost-effective manner.

SUMMARY OF THE INVENTION

In one embodiment, the present invention provides a system in which a phantom with X-ray positive marks and marks detectable by a position detection system remains connected to the subject of the investigation during the entire procedure and a volume data set of the investigated region is generated during the operation by means of the X-ray diagnostic machine. During a scan to take a series of 2D projection images of varying projection geometry for the subsequent 3D volume reconstruction, suitable fixation means ensure that the phantom and the investigation subject do not change their position in space. The positions of the X-ray positive marks in the 2D X-ray projection images are determined by an evaluation program in the image processing computer of the X-ray diagnostic machine, and from this is found a protocol for the transformation of each individual 2D data set. The transformed 2D data sets are used for the reconstruction of a volume data set and relayed to the navigation system. The navigation of an instrument occurs by this method in a reconstructed volume of high precision, whose data set is calculated from a series of superimposed 2D X-ray projections of the subject and the phantom. From comparison of the 2D projection of the phantom with the kinematic data stored in the X-ray diagnostic machine, each 2D projection is transformed by known techniques. The transformation in the simplest case may comprise a displacement of the original 2D projection by a displacement vector in the plane of the entry window of the X-ray receiver. For the back calculation of the projection geometry, it may be necessary or advisable on account of the nature of the phantom to make certain assumptions. Thus, one assumption might be: the position of the entry window of the X-ray receiver is determined with the aid of correction tables obtained from the kinematics in a calibration run, and the displacements of the image of the phantom in the 2D projection are assigned exclusively to the displacement of the focal spot of the X-ray source. Another assumption might be: the deviations of the 2D projection of the phantom from the value calculated from kinematics are divided equally between the X-ray receiver and the X-ray source. Furthermore, certain embodiments of the invention calls for saving in tables of values of the image processing computer the distributions of the magnitude of the deviation of the positions of the X-ray source and the X-ray receiver, depending on the adjustments of the axes of the X-ray diagnostic machine.

In a preferred embodiment, the greater the number of X-ray positive marks detected in the operating field, the more complex the transformations may become: for example, image magnification, image distortion, or the like. It has been found in practice that simply factoring in a single X-ray positive mark for the transformation of the 2D projections provides a substantial improvement in the quality of the 3D data set.

DETAILED DESCRIPTION OF THE PREFERRED EMBODIMENT

Figure 1:
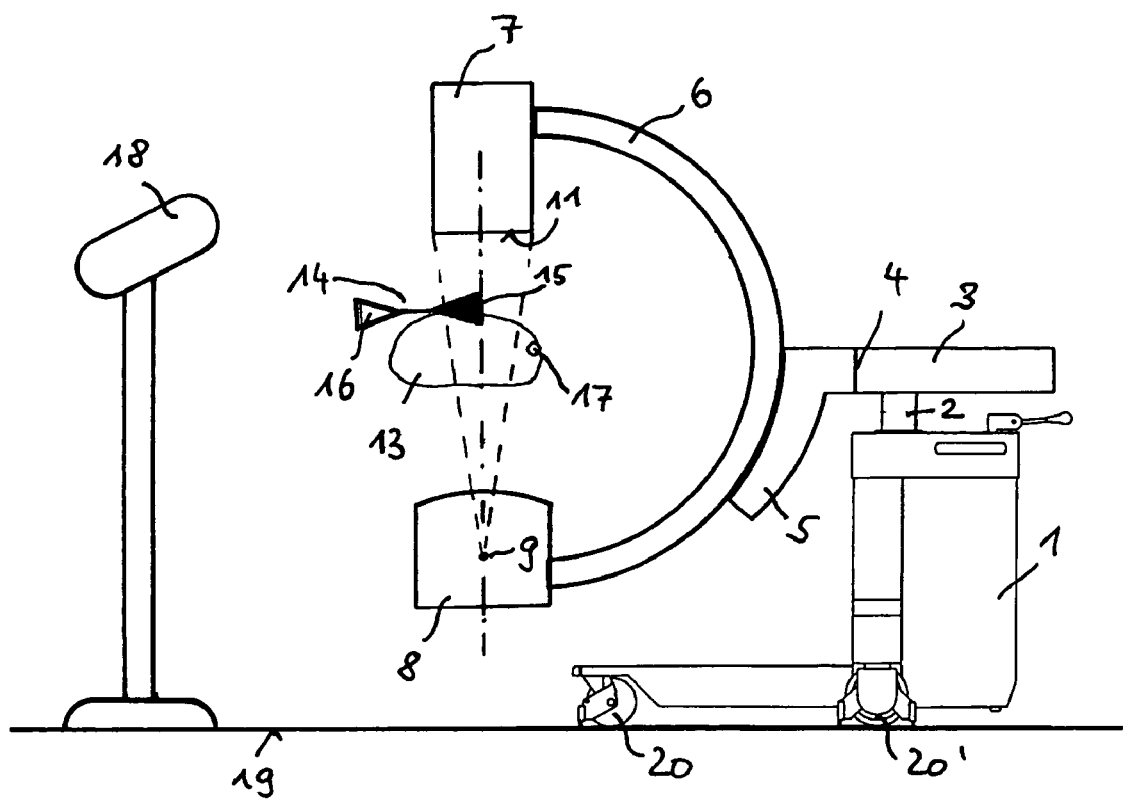
FIG. 1 schematically illustrates a mobile X-ray diagnostic system of one embodiment.

FIG. 1 shows a mobile X-ray diagnostic machine with an instrument cart 1 able to move on rollers 20, 20' along the floor 19, carrying a C-arm 6 capable of multiple adjustments. The X-ray source 8 and the X-ray receiver 7 are arranged at the ends of a C-arm 6, which is mounted in a C-arm support 5 and able to move about its midpoint 17 along its circumference. The C-arm support 5 is arranged on the instrument cart 1 and capable of multiple adjustments. The C-arm support 5 is mounted by a swivel bearing 4 on a horizontal guide 3 and able to swivel about a horizontal axis. The horizontal guide 3 is mounted on a column 2, able to adjust its height and to pivot about the vertical axis of the column 2. Preferably, all adjustment mechanisms of the C-arm 6 are outfitted with position-measuring sensors, whose measurement values are sent to a central motion control system of the X-ray diagnostic machine. All axes of motion can be either individually or collectively halted by brakes. In particular, the rollers 20, 20' are outfitted with a parking brake. Preferably, the adjustment motion of the C-arm in the support (orbital motion), the adjustment in the horizontal guide 3 and the vertical adjustment in the column can be adjusted by electric motors, and the motors arranged in the adjustment axes are controlled by a central motion control unit of the X-ray diagnostic machine.

The position detection system 18 can be an optical (infrared) system, an electromagnetic system, or a system based on measuring a magnetic field.

The precision of the navigation with an instrument 14 that contains marks 16 which are detected by the position detection system is improved by the use of transformed 2D data sets for the volume reconstruction. In one embodiment, the present invention provides a system in which a phantom 15 with X-ray positive marks and marks detectable by a position detection system 18 remains connected to the subject 13 of the investigation during the entire procedure and a volume data set of the investigated region is generated during the operation by means of the X-ray diagnostic machine. During a scan to take a series of 2D projection images of varying projection geometry for the subsequent 3D volume reconstruction, suitable fixation means ensure that the phantom 15 and the investigation subject 13 do not change their position in space. The positions of the X-ray positive marks in the 2D X-ray projection images are determined by an evaluation program in the image processing computer of the X-ray diagnostic machine, and from this is found a protocol for the transformation of each individual 2D data set. The transformed 2D data sets are used for the reconstruction of a volume data set and relayed to the navigation system. The navigation of an instrument occurs by this method in a reconstructed volume of high precision, whose data set is calculated from a series of superimposed 2D X-ray projections of the subject and the phantom. From comparison of the 2D projection of the phantom with the kinematic data stored in the X-ray diagnostic machine, each 2D projection is transformed by known techniques. The transformation in the simplest case may comprise a displacement of the original 2D projection by a displacement vector in the plane of the entry window 11 of the X-ray receiver 7. For the back calculation of the projection geometry, it may be necessary or advisable on account of the nature of the phantom to make certain assumptions. Thus, one assumption might be: the position of the entry window of the X-ray receiver is determined with the aid of correction tables obtained from the kinematics in a calibration run. and the displacements of the image of the phantom in the 2D projection are assigned exclusively to the displacement of the focal spot 9 of the X-ray source 8. Another assumption might be: the deviations of the 2D projection of the phantom from the value calculated from kinematics are divided equally between the X-ray receiver 7 and the X-ray source 8. Furthermore, certain embodiments of the invention calls for saving in tables of values of the image processing computer the distributions of the magnitude of the deviation of the positions of the X-ray source 8 and the X-ray receiver 7, depending on the adjustments of the axes of the X-ray diagnostic machine.

Although the foregoing description of the preferred embodiments of the present invention has shown, described and pointed out the fundamental novel features of the invention, it will be understood that various omissions, substitutions, and changes in the form of the detail of the invention as illustrated as well as the uses thereof, may be made by those skilled in the art, without departing from the spirit of the invention. Particularly, it will be appreciated that the preferred embodiments of the invention may manifest itself in other shapes and configurations as appropriate for the end use of the article made thereby.

What is claimed is:

1. A method for improving volume reconstruction in navigationally guided operations on a subject of investigation, making use of an X-ray diagnostic machine with an X-ray receiver, an X-ray source, an image processing computer, a position detection system, and a phantom, which contains X-ray positive marks and marks detectable by the position detection system in a fixed spatial relation, comprising:

arranging the phantom on the subject in a region being explored in a manner such that the phantom remains rigidly connected to said subject during the entire operation and remains fixed in space during each scan;

using the X-ray diagnostic machine to create a series of 2D projection images of the region being explored with different projection geometries, each projection containing at least some of the X-ray positive marks of the phantom;

determining the positions of the X-ray positive marks on the phantom from the 2D projection images obtained from each scan in the image processing computer; and comparing the positions of the X-ray positive marks on the phantom with the calculated nominal positions of the X-ray positive marks for each scan determined by the position detection system, thus calibrating and transforming each 2D projection image to a transformed 2D data set in a manner such that the sum of deviations between the positions of the X-ray positive marks determined from the 2D projection image and the positions of the X-ray positive marks in the transformed 2D data set is minimized and any deviation of the 2D projection of the phantom from the value calculated from kinematics is divided equally between the X-ray receiver and the X-ray source; and reconstructing a volume with the transformed 2D data sets.

2. The method according to claim 1, wherein the reconstructed volume data of an X-ray volume, relative to a system of coordinates connected to the X-ray positive marks of the phantom, are relayed to the navigation system.

* * * * *